(12) United States Patent
Santala (10) Patent No.: US 10,357,174 B1
(45) Date of Patent: Jul. 23, 2019

(54) ADJUSTABLE LEADWIRE DEVICE FOR PATIENT PHYSIOLOGICAL MONITORING AND METHODS FOR MAKING THE SAME

(71) Applicant: General Electric Company, Schenectady, NY (US)

(72) Inventor: Robert Filip Arnold Santala, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/940,595

(22) Filed: Mar. 29, 2018

(51) Int. Cl.
*A61B 5/0432* (2006.01)
*A61B 5/0408* (2006.01)
*A61B 5/00* (2006.01)
*A61B 5/0456* (2006.01)
*A61B 5/0472* (2006.01)
*A61B 5/0468* (2006.01)

(52) U.S. Cl.
CPC .......... *A61B 5/0432* (2013.01); *A61B 5/0006* (2013.01); *A61B 5/04085* (2013.01); *A61B 5/683* (2013.01); *A61B 5/0456* (2013.01); *A61B 5/0468* (2013.01); *A61B 5/0472* (2013.01)

(58) Field of Classification Search
CPC .......................... A61B 5/0432; A61B 5/0006
USPC ................................................ 439/502, 909
See application file for complete search history.

(56) References Cited

U.S. PATENT DOCUMENTS 5,366,493 A * 11/1994 Scheiner .................. A61N 1/05
                                                              607/116
6,377,845 B1   4/2002 Kinast
(Continued)

FOREIGN PATENT DOCUMENTS

EP         1359842 B1    5/2009
EP         2559280 A1    2/2013
(Continued)

OTHER PUBLICATIONS

Pending U.S. Appl. No. 14/586,393, filed Dec. 30, 2014, "Common Display Unit for a Plurality of Cableless Medical Sensors", Muuranto.
(Continued)

*Primary Examiner* — Tulsidas C Patel
*Assistant Examiner* — Peter G Leigh
(74) *Attorney, Agent, or Firm* — Andrus Intellectual Property Law, LLP (57) ABSTRACT

An adjustable leadwire device for connecting at least one surface electrode to a physiological monitor includes a length of insulated wire between a first attachment end and a second attachment end. The first attachment end includes a first connection means configured to conductively connect to the surface electrode and the second attachment end includes a second connection means configured to conductively connect to the physiological monitor. At least a portion of the length of insulated wire is coiled to form a helix. A sheath surrounds the helix and has a first end opening and a second opening. The sheath is configured such that coiled insulated wire is extendable out of at least one of the first end opening or the second end opening by pulling a respective one of the first attachment end and the second attachment end in order to adjust a length of the adjustable leadwire device.

20 Claims, 10 Drawing Sheets

(56) References Cited

U.S. PATENT DOCUMENTS

| | | | |
|---|---|---|---|
| 6,416,355 B1* | 7/2002 | Liao | H01R 13/6658 439/164 |
| 6,496,705 B1 | 12/2002 | Ng et al. | |
| 6,733,328 B2* | 5/2004 | Lin | H02G 11/02 439/501 |
| 6,749,566 B2 | 6/2004 | Russ | |
| 7,097,018 B2* | 8/2006 | Wu | B65H 75/4434 191/12.2 R |
| 7,357,666 B2* | 4/2008 | Wu | H01R 13/60 439/501 |
| 7,390,299 B2 | 6/2008 | Weiner et al. | |
| 8,180,425 B2* | 5/2012 | Selvitelli | A61B 5/04085 600/382 |
| 8,475,368 B2 | 7/2013 | Tran et al. | |
| 8,700,118 B2* | 4/2014 | Oster | A61B 5/0002 600/372 |
| 8,755,908 B2* | 6/2014 | Jadwizak | A61N 1/056 607/122 |
| 9,550,042 B2* | 1/2017 | Tanioka | A61M 25/0052 |
| 2004/0173003 A1 | 9/2004 | Ibane | |
| 2006/0136768 A1 | 6/2006 | Liu et al. | |
| 2006/0284621 A1 | 12/2006 | Doi | |
| 2008/0173463 A1* | 7/2008 | Yamada | H01B 7/06 174/69 |
| 2008/0284599 A1 | 11/2008 | Zdeblick | |
| 2009/0304217 A1* | 12/2009 | Thalheimer | H04R 5/02 381/334 |
| 2009/0318818 A1 | 12/2009 | Whitaker et al. | |
| 2010/0168605 A1 | 7/2010 | Aarts | |
| 2011/0066051 A1 | 3/2011 | Moon | |
| 2011/0077497 A1* | 3/2011 | Oster | A61B 5/0002 600/372 |
| 2011/0145894 A1 | 6/2011 | Morchon et al. | |
| 2012/0068855 A1 | 3/2012 | Matsumura | |
| 2012/0108917 A1 | 5/2012 | Libbus et al. | |
| 2013/0053674 A1 | 2/2013 | Volker | |
| 2013/0109927 A1 | 5/2013 | Menzel | |
| 2013/0289376 A1 | 10/2013 | Lang | |
| 2013/0337842 A1 | 12/2013 | Wang et al. | |
| 2014/0073895 A1* | 3/2014 | Freeman | A61B 5/04087 600/382 |
| 2014/0187883 A1 | 7/2014 | Lisogurski | |
| 2015/0116130 A1 | 4/2015 | Grubis | |

FOREIGN PATENT DOCUMENTS

| | | |
|---|---|---|
| EP | 1881784 B1 | 10/2013 |
| WO | 2014027273 A1 | 2/2014 |

OTHER PUBLICATIONS

Radius-7 brochure, Masimo, admitted prior art.

IntelliVue Cableless Measurement brochure, Philips, Jun. 2013.

http:/electronicdesign.com/power/lightning-bolts-defibrillators-and-protection-circuitry-save-lives.

Soundarapandian et al., "Analog Front-End Design for ECG Systems Using Delta-Sigma ADCs", Texas Instruments, SBAA160A, Mar. 2009, Revised Apr. 2010.

Torres, Bernat Albet., "Wireless System for the Measurement of Bioelectric Signals using Capacitive Electrodes", Universitat Politecnica de Catalunya.

International Search Report and Written Opinion for International Application No. PCT/US2017/066401 dated Feb. 23, 2018. 10 pages.

\* cited by examiner

ADJUSTABLE LEADWIRE DEVICE FOR PATIENT PHYSIOLOGICAL MONITORING AND METHODS FOR MAKING THE SAME

BACKGROUND

This disclosure generally relates to leadwires for medical monitoring systems, and more specifically to an adjustable leadwire device for connecting one or more surface electrodes to a physiological monitor and methods for making the same.

Electrocardiograms (ECGs) are graphic depictions of electrical activity in the heart, i.e. cardiac potentials. ECGs are produced by electrocardiographs which are available as stand alone devices, portable devices, and/or as integrated functions in various types of multi-vital sign monitoring devices. ECGs are depicted by time (ms) versus voltage (mV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient.

Respiration monitors are also available that use chest electrodes that are similar or identical to ECG electrodes. For example, respiration rate measurement may be determined using impedance pneumography, where a high-frequency A/C current is passed between at least two electrodes (often the right arm electrode and left arm electrode), including a driving electrode and a receiving electrode, on the patient's chest and an impedance between the electrodes is determined. Respiration is then monitored according to the changing impedance values as the patient breathes.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an adjustable leadwire device for connecting at least one surface electrode to a physiological monitor includes a length of insulated wire between a first attachment end and a second attachment end. The first attachment end includes a first connection means configured to conductively connect to the surface electrode and the second attachment end includes a second connection means configured to conductively connect to the physiological monitor. At least a portion of the length of insulated wire is coiled to form a helix. A sheath surrounds the helix and has at least one of a first end opening and a second opening. The sheath is configured such that coiled insulated wire is extendable out of at least one of the first end opening or the second end opening by pulling a respective one of the first attachment and the second attachment end in order to adjust a length of the adjustable leadwire device.

In another embodiment, an adjustable leadwire device for connecting a physiological monitor to at least two surface electrodes includes a first length of insulated wire between a first attachment end and a second attachment end and a second length of insulated wire between a third attachment end and a fourth attachment end, wherein at least a portion of each of the first length of insulated wire and the second length of insulated wire are coiled together so as to form a helix. Each of the first attachment end and the third attachment end including a first connection means configured to conductively connect to a respective surface electrode. The second attachment end and the fourth attachment end both connect to a second connection means configured to conductively connect to the physiological monitor. A sheath surrounds the helix, the sheath having at least one of a first end opening and a second end opening, and wherein the length of the adjustable leadwire device is adjustable by extending both first and second coiled insulated wires out of at least one of the first end opening or the second end opening of the sheath.

One embodiment of a method of making an adjustable leadwire device for connecting at least one surface electrode to a physiological monitor includes providing a length of insulated wire, and coiling the length of insulated wire so as to form a helix having a helix length. The helix is then covered with a sheath such that the sheath maintains a diameter of the helix and at least substantially covers the helix length. The sheath is configured such that coiled insulated wire is extendable by pulling a respective one of the first attachment end and the second attachment end in order to adjust the length of the adjustable leadwire device.

Another embodiment of a method of making an adjustable leadwire device for connecting at least one surface electrode to a physiological monitor includes providing a length of insulated wire with a first end and a second end, and coiling at least a portion of the length of insulated wire so as to form a helix. A sheath is then applied around the helix, the sheath having a first end opening and a second end opening and positioned such that the first end of the length of insulated wire extends out of the first end opening of the sheath and the second end extends out of the second end opening of the sheath. A first connection means is formed on the first end of the length of insulated wire to create a first attachment end configured to conductively connect to the surface electrode, and a second connection means is formed on the second end of the length of insulated wire to create a second attachment end configured to conductively connect to the physiological monitor. The sheath is configured such that coiled insulated wire is extendable out of at least one of the first end opening or the second end opening of the sheath by pulling a respective one of the first attachment end and the second attachment end in order to adjust a length of the adjustable leadwire device.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Currently available ECG monitoring systems and methods typically include one-size-fits-all leads having an electrode at the end of a long leadwire. Since only one size leadwire is provided, they are designed to accommodate worst case scenario situations where long leadwires are required, and thus the leadwires often are much longer than needed for a given patient monitoring application. The excessively long leadwires often hinder patient movement, as patient movement often results in entanglement in the leadwires and dislodging one of the electrodes. Excessively long leadwires are also problematic for the nursing staff, because the leadwires and/or electrodes become detached from the patient during care operations, such as turning the patient or rearranging the protective sheets in operating room, etc. Furthermore, excessively long leadwires can lead to the introduction of unnecessary noise into the recorded signals.

In view of the foregoing problems and challenges with currently available ECG sensors and monitoring systems, the inventor developed the adjustable ECG sensors and leadwire sets, and related methods, disclosed herein. Specifically, the present inventor endeavored to develop an ECG sensor having an adjustable leadwire, where the leadwire can be sized to fit exactly to an arrangement of electrodes assembled on a patient, thereby eliminating entanglement problems, excess noise, etc. Specifically, the disclosed adjustable leadwire device can be expanded to the exact length needed for connecting a surface electrode to a physiological monitor.

Figure 1A:
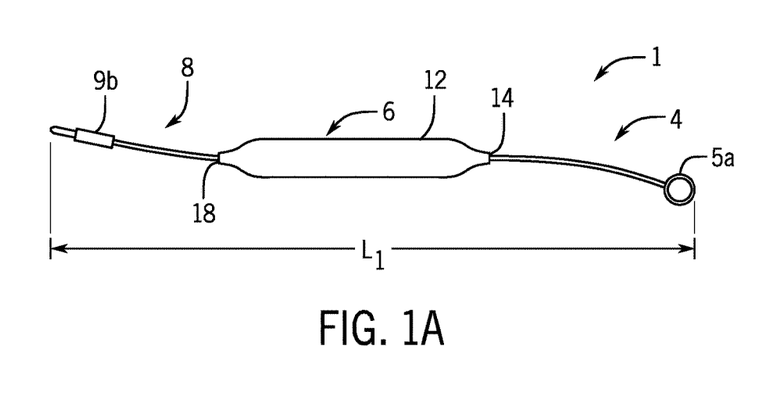
FIGS. 1A and 1B depict one embodiment of an adjustable leadwire device for connecting a physiological monitor and surface electrode.
Figure 1B:
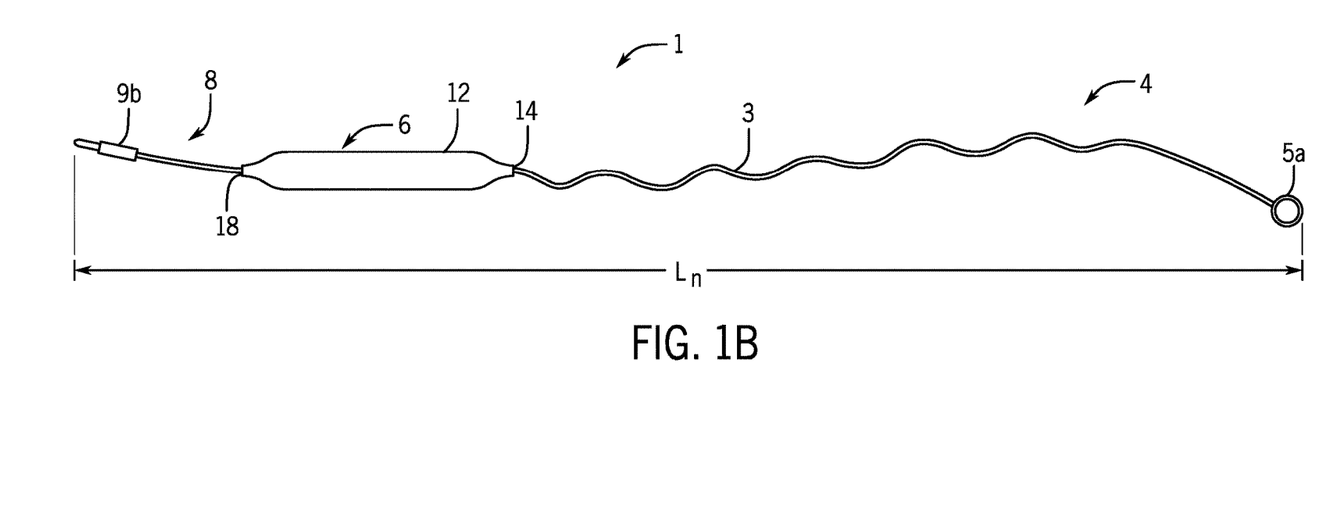
Figure 13:
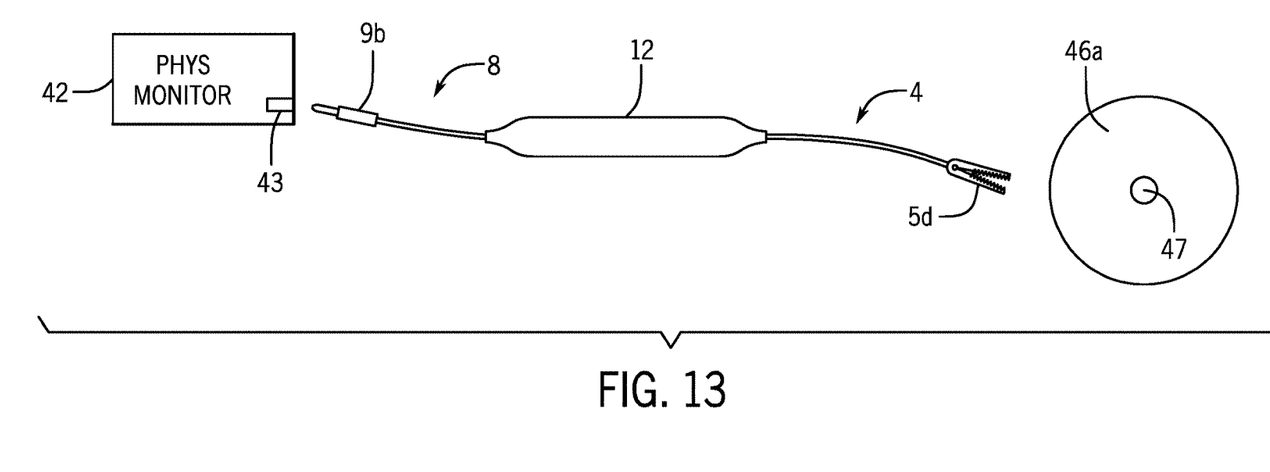
FIG. 13 depicts another exemplary embodiment of an adjustable leadwire device for connection between a physiological monitor and a surface electrode.
Figure 14:
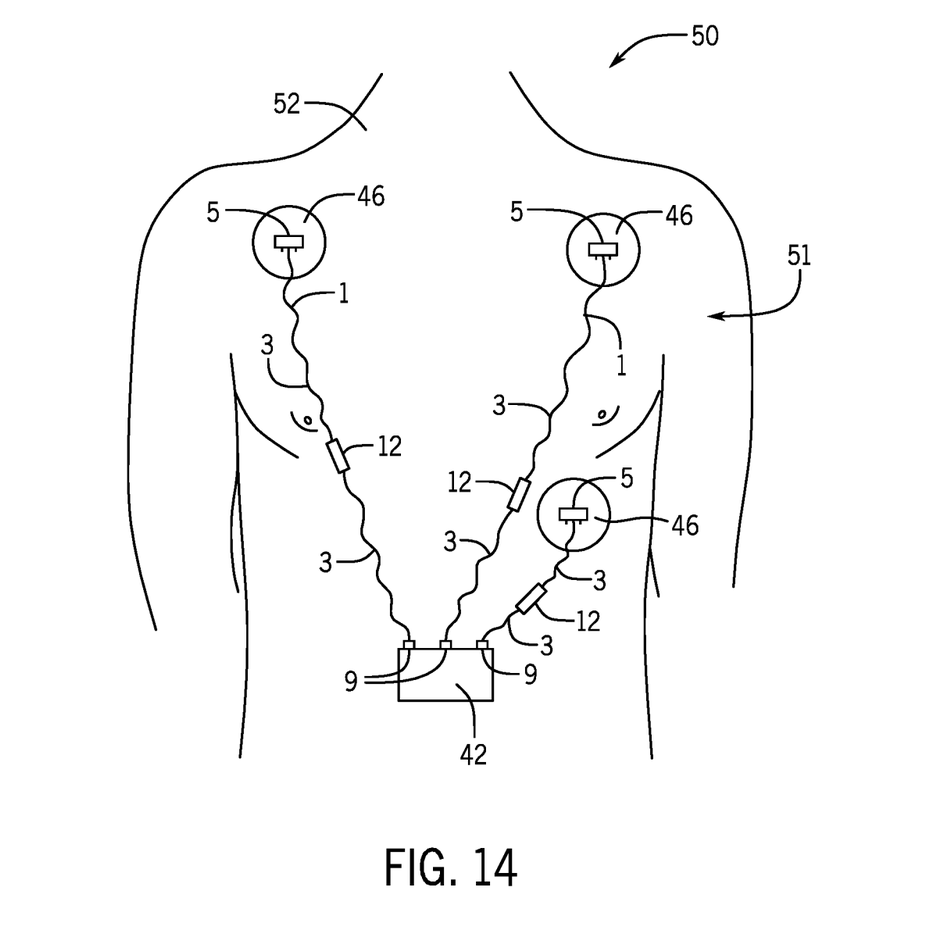
FIG. 14 depicts a physiological monitoring system in use on a patient, the physiological monitoring system having exemplary adjustable leadwire devices connecting surface electrodes to an ECG monitor.

FIGS. 1A and 1B depict an exemplary embodiment of the adjustable leadwire device 1 which has an initial length $L_1$ and is expandable to any length $L_n$ between the initial length $L_1$ and a fully expanded length $L_2$. This references also to FIGS. 2A and 2B, the adjustable leadwire device 1 is generally comprised of a length of insulated wire 2 coiled to form a helix 6. A sheath 12 surrounds the helix 6, which provides a form that maintains the helix diameter. The sheath 12 has a cylindrical shape with a first end opening 14 and a second end opening 18. A first attachment end 4 includes a first connection means 5 configured to conductively connect to a surface electrode. A second attachment end 8 includes a second connection means 9 configured to conductively connect to a physiological monitor, thereby to transmit physiological potentials and/or patient data from the electrode to the physiological monitor. FIGS. 13 and 14 exemplify such connections and are discussed in more detail herein.

The sheath 12 protects and maintains the helix, preventing the wire from extracting unintentionally. Additionally, the sheath 12 prevents the coiled leadwire from catching on the patient's skin and hair, and from catching on surrounding objects, and also provides a more finished look for the resulting lead product. Moreover, the sheath 12 limits the spring force of the coiled leadwire 3 pulling on the electrode, which may otherwise cause interference in the recorded physiological signal.

The sheath 12 is configured such that coiled insulated wire 3 comprising part of the helix 6 is extendable out of at least one of the first end opening 14 or the second end opening 18 by pulling the respective one of the first attachment end 4 and the second attachment end 8 in order to adjust the length $L_n$ of the adjustable leadwire device 1 so that it can be perfectly sized to provide connection between the surface electrode 46 and the physiological monitor 42 so as to avoid the above-discussed problems of entanglement, excessive noise, etc. The design also provides a convenient and compact leadwire device that is easy for a clinician to transport and use in a clinical environment. In certain embodiments, the sheath 12 is formed around the ends of the helix 6 in order to contain the coiled insulated wire 3 inside the sheath 12 until sufficient force is applied to either one or both of the attachment ends 4, 8 in order to pull coiled insulated wire 3 out of the sheath 12. In one embodiment, when the adjustable leadwire device 1 is in a fully collapsed form, the first attachment end 4 the extends out of the first end opening 14 and the second attachment end 8 extends out of the second end opening 18 of the sheath 12.

Depending on the diameter of the helix 6, the initial length $L_1$ of the adjustable leadwire device 1 may be quite short compared to its maximum length $L_2$. For example, the initial length $L_1$ may be 10% or less of the maximum length $L_2$, and the adjustable leadwire device 1 may be adjusted to any length $L_n$ therebetween. In various embodiments, the length $L_n$ of the adjustable leadwire device 1 may be adjusted by pulling on either one of the first attachment end 4 or the second attachment end 8, such that the coiled insulated wire 3 is extendable out of either side of the sheath 12. In other embodiments, one side of the adjustable leadwire device may be fixed, such that the length $L_n$ may only be adjusted by pulling on a particular one of the first attachment end 4 or the second attachment end 8. In FIG. 1B, for example, the first attachment end 4 is extended out of the sheath 12 to extend the adjustable leadwire device 1 to a length $L_n$. FIG. 14 depicts exemplary adjustable leadwire devices 1 extended to various lengths depending on the distance between the electrode 46 on the patient and the physiological monitor 42. In the embodiment of FIG. 14, coiled insulated wire 3 is extended out of both sides of the sheath 12 of each adjustable leadwire device 1.

Figure 12:
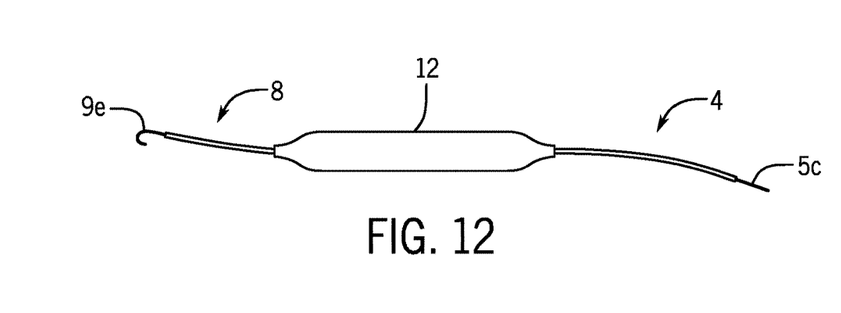
FIG. 12 depicts another exemplary embodiment of an adjustable leadwire device.
Figure 15:
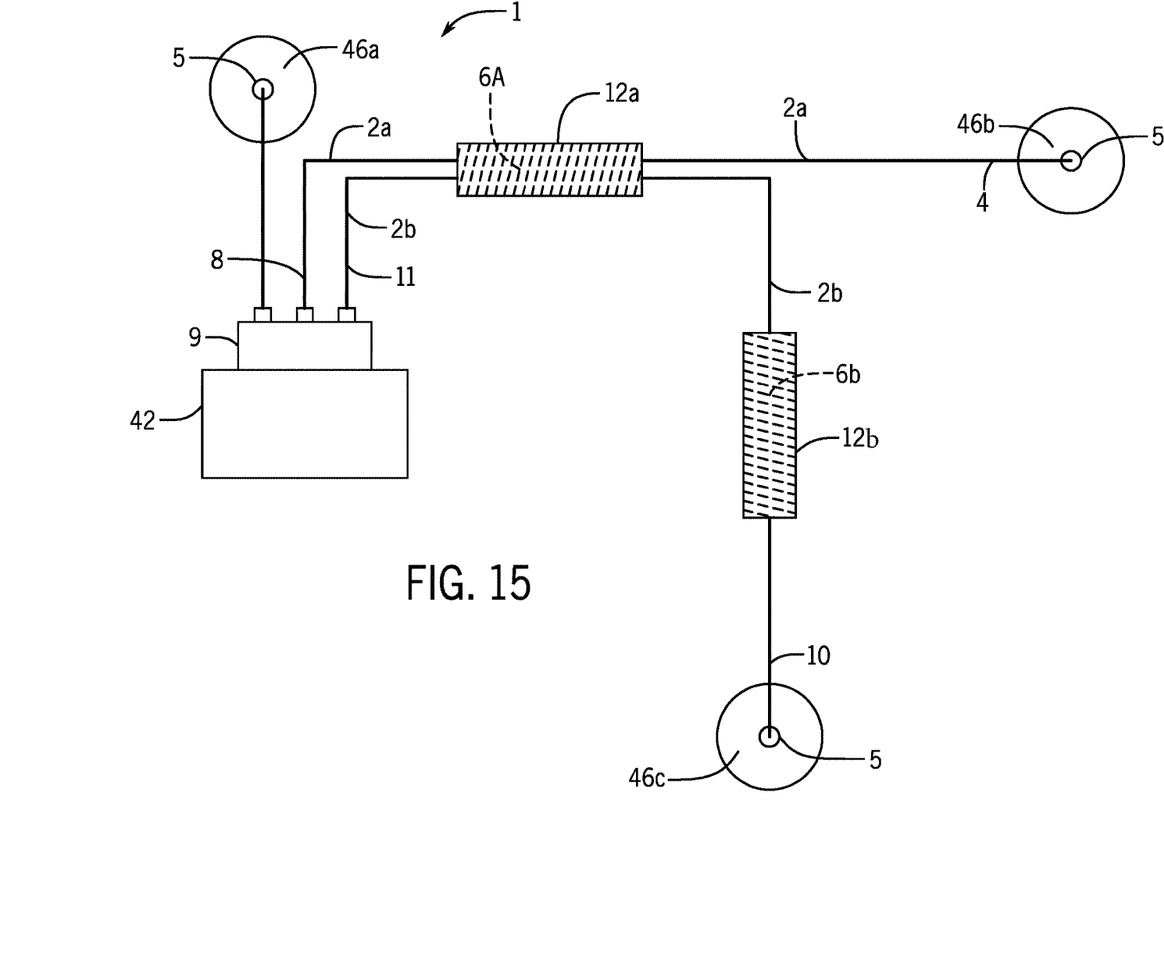
FIG. 15 depicts a physiological monitoring system having another embodiment of adjustable leadwire devices connecting surface electrodes to a patient monitor.

In various embodiments, the first connection means 5 and the second connection means 9 may be any device or element that enables or allows connection to the respective surface electrode 46 and physiological monitor 42. In certain embodiments, the first connection means 5 and the second connection means 9 may be identical to one another and interchangeable, such that each end can connect to either one of the surface electrode 46 and the physiological monitor 42. In other embodiments, the first connection means 5 may be different from the second connection means 9. In the examples depicted in FIGS. 1A and 1B, the first connection means 5a is a snap configured to connect to a snap electrode 46, such as the snap electrode 46a depicted in FIG. 13. Such snap connection means 5a are well known in the art of patient monitoring. The second connection means 9 in the embodiment of FIGS. 1A and 1B is a pin connector 9a configured to be inserted into a receiving port 44 of a patient monitor 42. Such pin connectors 9a are also well known in the patient monitoring arts. However, the first connection means 5 and the second connection means 9 may take any other form, such as any fastener or connector element known or available that is suitable for providing a conductive connection between the insulated wire 2 and the surface electrode 46 or physiological monitor 42. FIGS. 12 and 13 provide additional exemplary connection means 5, 9, which may include a clip 5d, such as an alligator clip that clips on to a conductive element in the electrode 46 (or on the physiological monitor 42). Other exemplary connection means include a hook 9e, capable of hooking to a conductive element on the patient monitor 42 (or the electrode 46). In still other embodiments, the connection means 5, 9 may simply be exposed wire 5c that can be received by or otherwise connected to the respective electrode 46 or patient monitor 42. For example, the exposed wire 5c may be permanently and galvanically connected to an electrode 46 as part of the manufacturing process of the adjustable leadwire device 1, such as by welding, solder, conductive glue, etc. FIG. 15 provides one example of such an embodiment. In such an embodiment, the device supplied to the end user includes the adjustable leadwire device 1 with an electrode 46 connected to one end and a second connection means, such as a pin connector 9b or other connector device, on the other end for connection to the patient monitor 42. Alternatively, the second connection means 9 may be exposed wire that is permanently connected (e.g. soldered) onto a printed circuit board comprising a patient monitor, or a portion thereof.

Figure 2A:
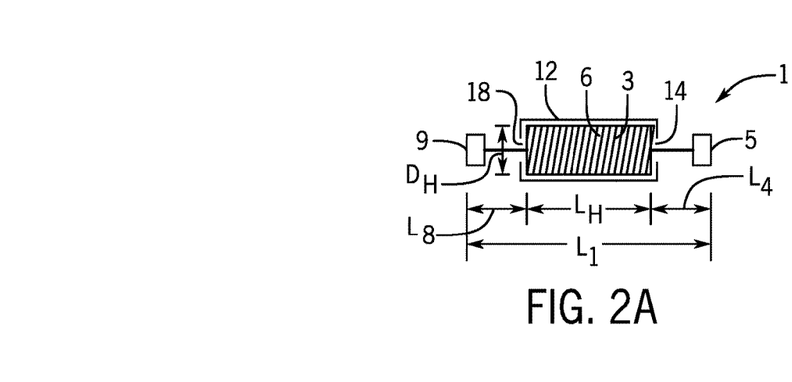
FIGS. 2A and 2B schematically depict another embodiment of an adjustable leadwire device.
Figure 2B:
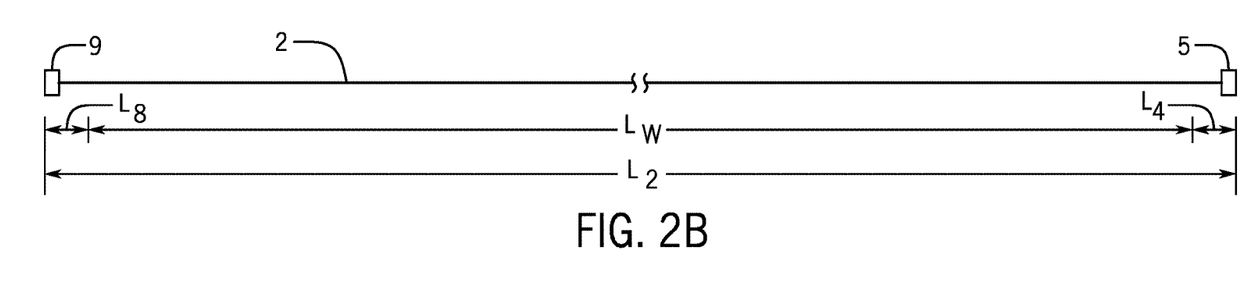

As exemplified in FIGS. 1A and 2A, in its fully retracted position the adjustable leadwire device 1 has an initial length $L_1$, wherein the coiled insulated wire 3 is entirely within the sheath 12. One or both of the attachment ends 4, 8 may be pulled to extend the length $L_n$ of the adjustable leadwire device 1, extending some or all of the coiled insulated wire 3 out of the first opening 14 or the second end opening 18 of the sheath 12. The adjustable leadwire device 1 has a maximum length $L_2$ to which the device can be extended. In certain embodiments, the coiled leadwire 3 may be fully extendable to a maximum length $L_2$ equal to the full, straight extension of the coiled leadwire 3 such that the helix 6 is completely eliminated. In such an embodiment, the maximum length $L_2$ is equal to the length $L_w$ of the insulated wire 2 plus a length of the first attachment end $L_4$ and a length of the second attachment end $L_8$.

The adjustable leadwire device 1 is created by coiling at least a portion of the length $L_w$ of insulated wire 2 into a helix 6. In certain embodiments, the insulation material on the insulated wire can be chosen based on desired properties. For example, a silicone covered wire is "stickier" and thus needs a larger pulling force to extend. The sheath 12 material may also be chosen based on similar properties and to appropriately interact with the wire insulation material so as to achieve the proper pulling force for extending the coiled leadwire out of the helix. As exemplified in FIG. 3, the helix may be created by wrapping the insulated wire 2 around a support bar 2. Once the helix is created, the length $L_w$ of insulated wire 2 is much shorter. In one example, the initial length $L_1$ is less than or equal to 5% of the maximum length $L_2$. In another example, the initial length $L_1$ is less than or equal to 10% of the maximum length $L_2$. In yet other examples, the initial length $L_1$ is less than or equal to 15% of the maximum length $L_2$, less than or equal to 20% of the maximum length $L_2$, or less than or equal to 25% of the maximum length $L_2$. To provide further explanatory examples, the initial length $L_1$ may be in the range of 1 cm-3 cm, and the maximum length $L_2$ may be in the range of 16 cm-48 cm. In other embodiments, the initial length $L_1$ and the maximum length $L_2$ may have different proportions, which will depend on the relative proportion of the length $L_w$ of insulated wire 2 that is coiled into the helix 6 and the diameter $d_H$ of the helix 6. The insulated wire 2 may be wound into a helix 6 of any diameter $d_H$ that provides a convenient and well sized resulting device 1. In exemplary embodiments, the diameter $d_H$ may be in the range of 5 mm-10 mm, such as approximately 8 mm. If the entire length $L_w$ is coiled, then the entire length $L_w$ of insulated wire only occupies length $L_H$ of the helix. In other embodiments, such as that exemplified at FIG. 15, only a portion of the length $L_w$ of the insulated wire 2 is coiled into one or more helixes 6. The helix length $L_H$ of the helix 6 is surrounded by the sheath 12, which is sized appropriately in order to maintain the diameter $d_H$ of the helix 6.

Figure 3:
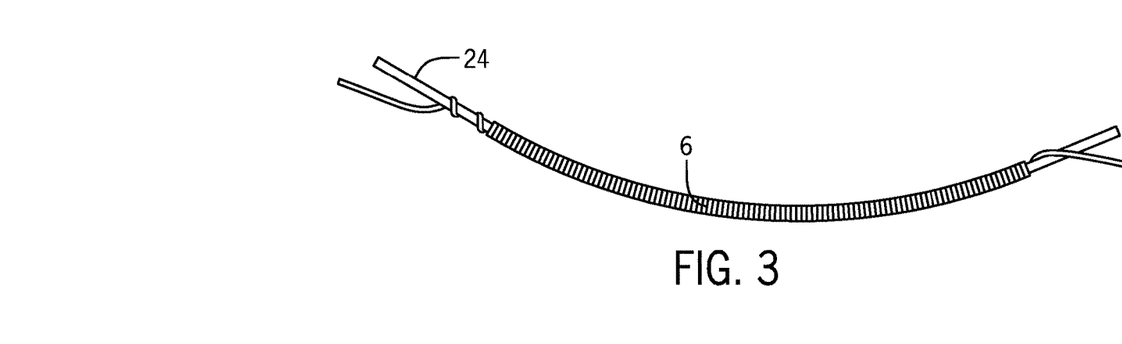
FIG. 3 depicts an exemplary step for making an embodiment of an adjustable leadwire device according to the present disclosure.
Figure 4A:
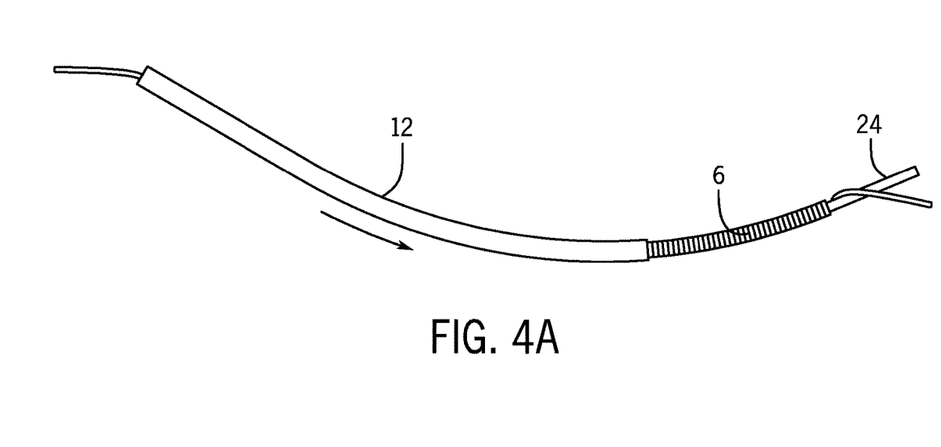
FIGS. 4A and 4B depict further exemplary steps for making an embodiment of an adjustable leadwire device according to the present disclosure.
Figure 4B:
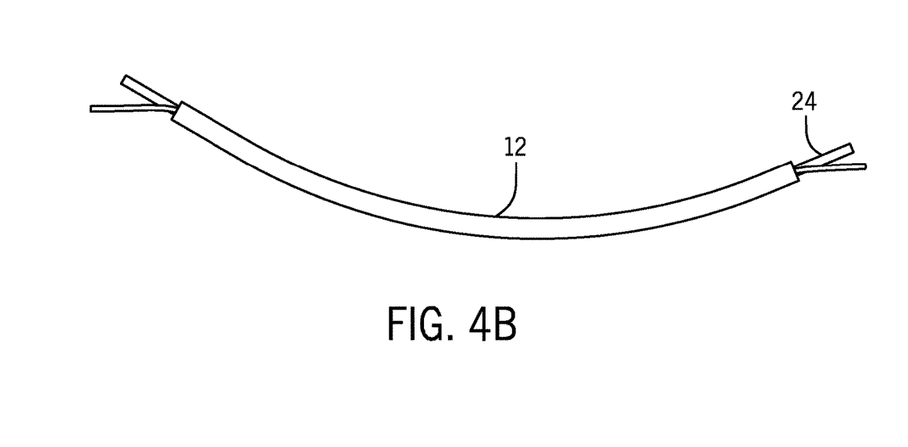
Figure 5:
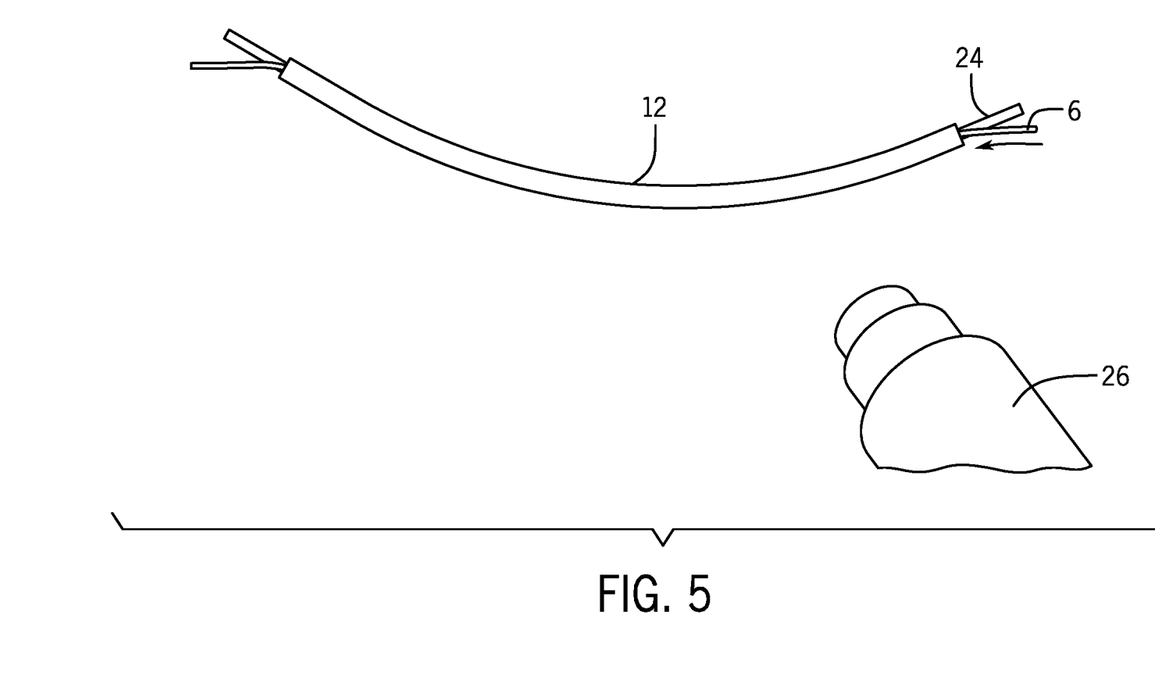
FIG. 5 depicts a further exemplary step for making an embodiment of an adjustable leadwire device according to the present disclosure.

FIGS. 3-11 depict an exemplary method of making an adjustable leadwire device 1. FIG. 3 depicts an initial length of leadwire coiled around a support bar 24 in order to form the helix 6. In various embodiments, the length of leadwire may be the length needed for manufacturing a single adjustable leadwire device 1 or multiple adjustable leadwire devices that may be cut during the manufacturing process. In the depicted example, an extended length of insulated wire 2 is wrapped around a support bar 24 to form a single helix 6 that is then cut into sections during the manufacturing process, wherein each section becomes an adjustable leadwire device 1. The extended helix 6 is then covered by an appropriate length of sheath 12 that covers most or all of the length of the extended helix 6. The sheath may be applied around the helix 6 by various application methods. In the exemplary embodiment shown in FIGS. 4A and 4B, the sheath 12 may be plastic tubing sized to surround the helix 6, and thus to slide over the helix 6 and the support bar 24. In one example, the sheath 12 may be comprised of heat shrinkable plastic tubing. In such an embodiment depicted in FIG. 5, a heat source 26 may be applied to the sheath-covered helix 6 in order to shrink the diameter of the sheath 12 to fit tightly around the diameter $d_H$ of the helix 6. Depending on the material and size of the heat shrinkable plastic tubing, an initial amount of heat is applied so as not to shrink the sheath 12 too tightly around the helix 6 that would prevent extension of the coiled insulated wire 3 from the sheath 12. In other embodiments, the sheath 12 may be a plastic or cloth sheet or tape that is wrapped around the helix 6 with an appropriate tension so as to be able to retain the diameter $d_H$ of the helix 6. In still other embodiments, the sheath may be a lacquer or glue sprayed on the surface of the helix. In such an embodiment, the sheath would break as the wire is extended leaving no excess sheath after extension.

Figure 6:
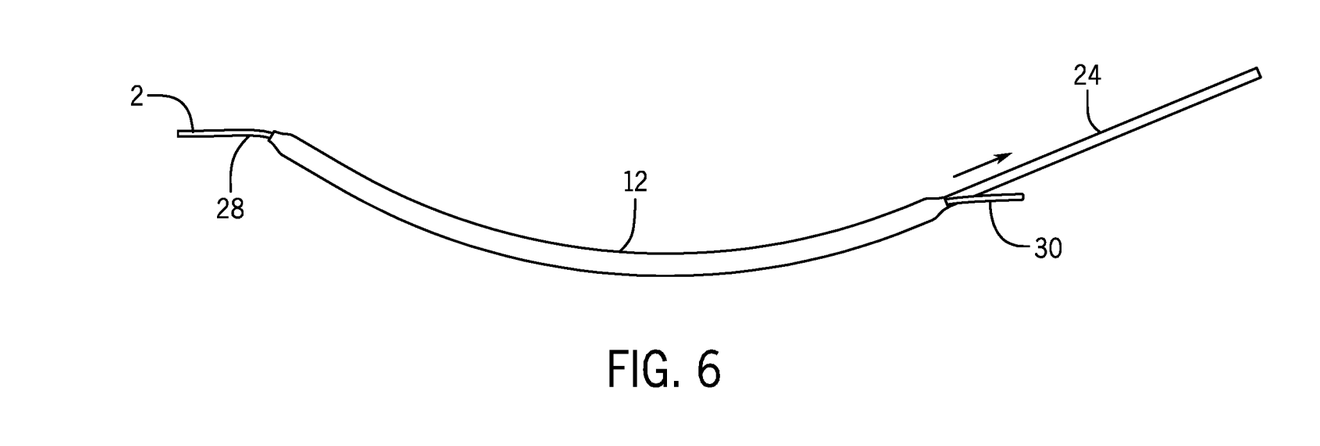
FIG. 6 depicts a further exemplary step for making an embodiment of an adjustable leadwire device according to the present disclosure.
Figure 7:
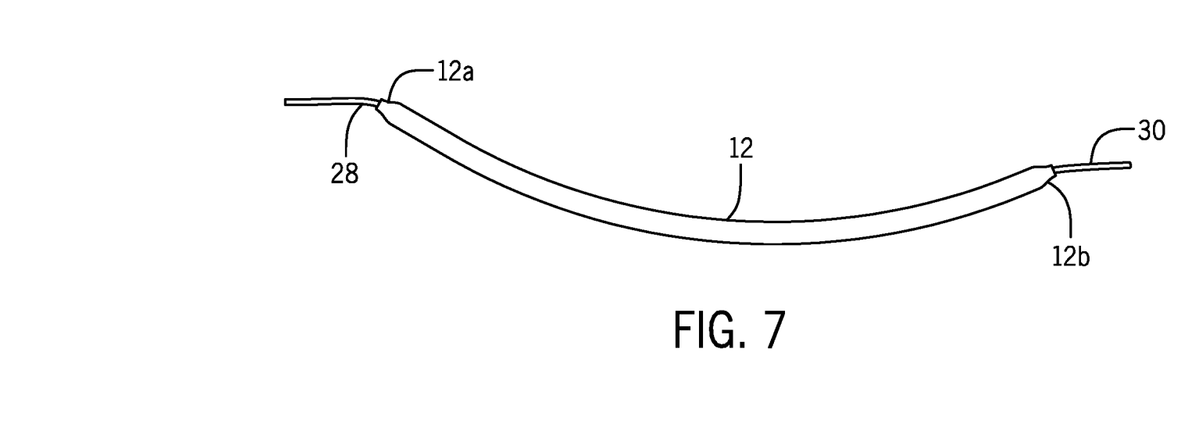
FIG. 7 depicts a further exemplary step for making an embodiment of an adjustable leadwire device according to the present disclosure.
Figure 8A:
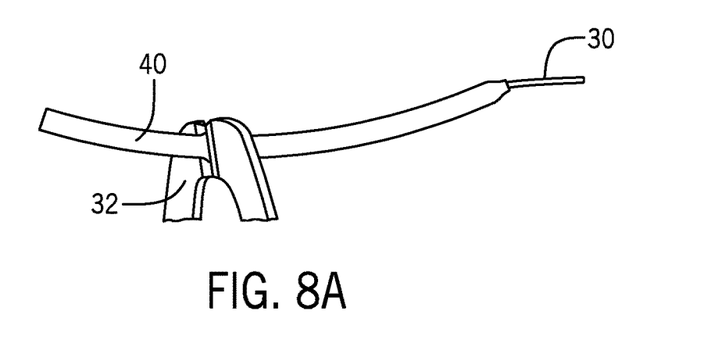
FIGS. 8A and 8B depict further exemplary steps for making an embodiment of an adjustable leadwire device according to the present disclosure.
Figure 8B:
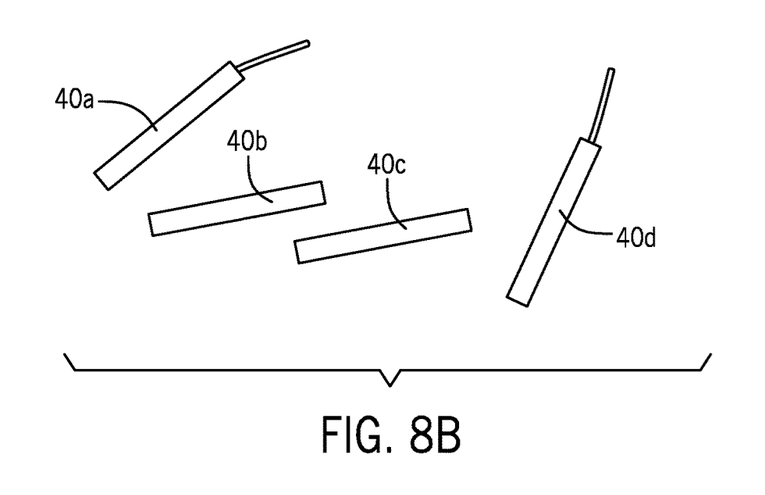
Figure 9:
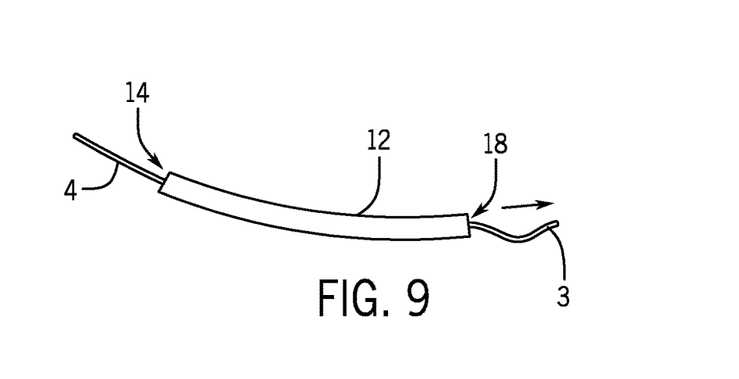
FIG. 9 depicts a further exemplary step for making an embodiment of an adjustable leadwire device according to the present disclosure.

As shown in FIG. 6, the support bar 24 is removed from the interior of the helix 6 after the sheath 12 is applied. In certain embodiments, ends 28, 30 of the uncoiled insulated wire 2 may extend from the open ends of the sheath 12. FIG. 7 depicts an extended length of helix covered in the sheath 12 with ends 28, 30 of uncoiled insulated wire 2 sticking out from the open ends 12a, 12b of the sheath 12. That extended length of sheath-covered helix 6 can then be cut into sections 40, as exemplified in FIG. 8A, in order to form separate adjustable leadwire devices 1. In various embodiments, each section 40 may have a different length depending on the minimum and maximum lengths $L_1$, $L_2$ needed for the adjustable leadwire device 1. FIG. 8B depicts the extended sheath-covered helix divided into four sections 40a-40d, wherein each section 40a-40d will become an adjustable leadwire device 1. The attachment ends 4, 8 of the adjustable leadwire device 1 are formed by removing a portion of the coiled insulated wire 3 from a respective end opening 14, 18 of the sheath 12. Namely, the coiled insulated wire may be grabbed, such as with a plyer or tweezer tool, and pulled a certain distance and straightened in order to form the respective attachment end 4, 8.

Figure 10:
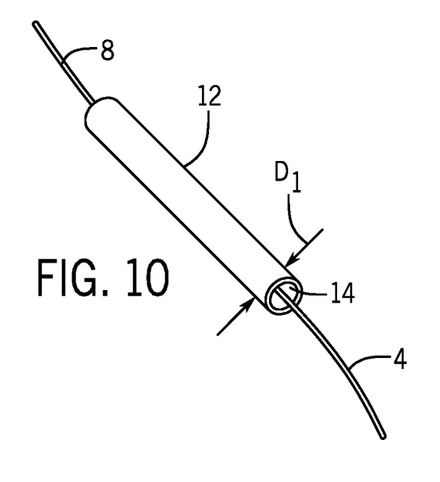
FIG. 10 depicts a further exemplary step for making an embodiment of an adjustable leadwire device according to the present disclosure.
Figure 11:
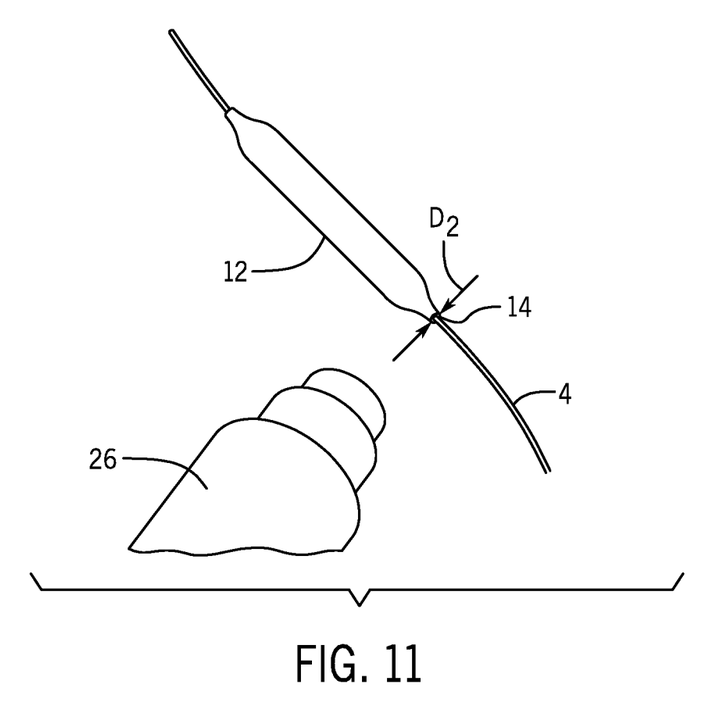
FIG. 11 depicts a further exemplary step for making an embodiment of an adjustable leadwire device according to the present disclosure.

As shown in FIGS. 10-11, the end openings 14, 18 of the sheath 12 may be formed around the helix 6 in order to retain the helix 6 inside the sheath 12. In the example where the sheath 12 is comprised of heat shrinkable plastic tubing, heat may again be applied to shrink the diameter of the sheath 12 from a first diameter $d_1$ to a second diameter $d_2$. The amount of heat applied to the ends of the sheath is configured appropriately so that the resulting diameter $d_2$ is configured to allow extension of the coiled insulated wire 3 by an appropriate pull force. Thus, the force required to extend the adjustable leadwire device 1 can be controlled by appropriately sizing the diameter $d_2$ so that it is durable and does not overly extend to easily when the clinician is using it, but is not overly restrictive to require too much force.

FIGS. 13, 14, and 15 depict embodiments of one or more adjustable leadwire devices 1 in use with a physiological monitor 46 for monitoring one or more physiological parameters from a patient. In various examples described herein, the adjustable leadwire devices 1 may be useful in connection with an ECG monitor or a respiration monitor, or other physiological monitor requiring several electrodes be connected to the patient at various distances from the physiological monitor. One or more adjustable leadwire devices 1 can be extended to an appropriate length to provide connection between each respective electrode 4 and the physiological monitor 42 in order to perfectly fit the patient with no excess leadwire posing an entanglement hazard. In various embodiments, the physiological monitor 42 may be a bedside device, or may be a wearable device attached to the patient's body. For example, the physiological monitor 42 may be an ECG monitor and/or respiratory monitor worn on the patient, such as attached to the patient by a band extending around the patient's chest, abdomen, or waist.

FIG. 14 depicts one embodiment of the physiological monitoring system 50 arranged to obtain a three-lead ECG from a patient 52. Accordingly, the depicted embodiment includes a leadwire set 51 comprised of three adjustable leadwire devices 1 connected to an ECG monitor 42. Such arrangement is for the purposes of example only, and a person having ordinary skill in the art in light of the disclosure than any number of electrodes 46 and adjustable leadwire devices 1 may be employed in various arrangement in order to record ECGs, including various numbers of leads and/or to record other physiological parameters, such as patient respiration. As described above, the adjustable leadwire devices 1 are each connected to a surface electrode 46. Such connection may be permanent connection made at the manufacturing stage or may be a connection made by a clinician during system set up, such as by connecting the adjustable leadwire one to the surface electrode 46 via a snap 5a or a clip 5d. The opposing attachment ends connect to the physiological monitor 42 via attachment means 9, examples of which are described herein. Each of the adjustable leadwire devices 1 have been sized to fit the surface electrode arrangement on the patient—i.e., to connect between the physiological monitor 42 and the respective electrode 46—and thus the adjustable leadwire devices 1 are sized to the patient with no excess leadwire posing an entanglement hazard or collecting excess noise.

FIG. 15 depicts another embodiment of a physiological monitoring system 50 arranged to obtain a three-lead ECG (or, depending on configuration, to record another physiological parameter involving 3 chest electrodes, such as respiration) from a patient. In the depicted embodiment, the adjustable leadwire device 1 is configured to connect three surface electrodes 46a-46c to a physiological monitor 42. In the depicted embodiment, two insulated wires are coiled together to form a single helix 6a, from which both the first and second insulated wires are extendable. In the depicted embodiment, a first length of insulated wire 2a connects between a second electrode 46b and a connection means 9 at the physiological monitor 42. Specifically, the first insulated wire has a first attachment end 4 and second attachment end 8, as is described above. A second length of insulated wire 2b extends between a third electrode 46c and the connection means 9 to the patient monitor 42, the second insulated wire 2b having a third attachment end 10 connecting to the third electrode 46c and a fourth attachment end 11 connecting to the connection means 9 for connecting to the physiological monitor 42. A portion of each of the first insulated wire 2a and the second insulated wire 2b are coiled together to form a single helix 6a, which is covered in and contained inside the sheath 12a. Thus, first and second coiled insulated wires are extendable out of the helix 6a by pulling on either one or both of the first or second insulated wires 2a, 2b. Accordingly, the first and second insulated wires are extended simultaneously from the helix 6a. In other embodiments, the first and second insulated wires 2a and 2b may be coiled concentrically and arranged such that the wires are separately extendable from the sheath 12a.

In the embodiment depicted in FIG. 15, the second insulated wire 2b is longer than the first insulated wire 2a. The second insulated wire 2b is coiled to form a second helix 6b. Specifically, at least a portion of the remaining length of the second insulated wire 2b that is not coiled in the first helix 6a is further coiled to form a second helix 6b. The second helix 6b is covered in a second sheath 12b. The sheath 12b is configured as described above, such that the coiled second insulated wire 2b is extendable out of an end opening of the sheath, such as by pulling on the third attachment end 10. Thereby, the adjustable leadwire device 1 of FIG. 15 can be adjusted to separately customize the length between the patient monitor and each of the second electrode 46b and the third electrode 46c. In the depicted embodiment, the first electrode 46a connects to the physiological monitor 42 via a standard leadwire that is not adjustable in length. However, in other embodiments, a second adjustable leadwire device 1 may connect between the physiological monitor 42 and the first surface electrode 46a. In still other embodiments, a single adjustable leadwire device 1 may have a first helix comprised of three or more separate leadwires coiled together, which may have different lengths, and may be jointly coiled and extendable or separately coiled and separately extendable as described herein.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. An adjustable leadwire device for connecting a physiological monitor and at least one surface electrode, the adjustable leadwire device comprising:
   a length of insulated wire between a first attachment end and a second attachment end;
   the first attachment end including a first connection means configured to conductively connect to the surface electrode and the second attachment end including a second connection means configured to conductively connect to the physiological monitor;
   wherein at least a portion of the length of insulated wire is coiled so as to form a helix;
   a sheath surrounding the helix, the sheath having at least one of a first end opening and a second end opening;
   wherein the sheath is configured such that coiled insulated wire is extendable out of at least one of the first end opening or the second end opening by pulling a respective one of the first attachment end and the second attachment end in order to adjust a length of the adjustable leadwire device;
      wherein the adjustable leadwire device has an initial length when the coiled insulated wire is entirely within the sheath; and
      wherein the adjustable leadwire device is extendable to any length between the initial length and a maximum length, wherein the initial length is less than or equal to 10% of the maximum length.

2. The adjustable leadwire device of claim 1, wherein the maximum length is the length of insulated wire plus a length of the first attachment end and the second attachment end.

3. The adjustable leadwire device of claim 1, wherein at least one of the first connection means and the second connection means is exposed wire.

4. The adjustable leadwire device of claim 1, wherein at least one of the first connection means and the second connection means comprise a fastener that fastens to a conduction point on at least one of the physiological monitor or the electrode.

5. The adjustable leadwire device of claim 4, wherein the fastener comprises one of a clip, a snap, and a hook.

6. The adjustable leadwire device of claim 1, wherein at least one of the first connection means and the second connection means comprise a pin connector configured to be received by a receiving port in at least one of the physiological monitor or the surface electrode.

7. The adjustable leadwire device of claim 1, wherein the first connection means and the second connection means are identical.

8. The adjustable leadwire device of claim 1, wherein the sheath is heat shrinkable plastic tubing.

9. The adjustable leadwire device of claim 1, wherein the first attachment end extends out of the first end opening of the sheath and the second attachment end extends out of the second end opening of the sheath.

10. The adjustable leadwire device of claim 1, which is for connecting a physiological monitor and at least two surface electrodes, and further comprising
   at least a second length of insulated wire between a third attachment end and a fourth attachment end;
   the third attachment end including a first connection means configured to conductively connect to a second surface electrode and the fourth attachment end including a second connection means configured to conductively connect to the physiological monitor;
   wherein at least a portion of the second length of insulated wire is coiled with the first length of insulated wire so as to form the helix from both the first and second lengths of insulated wire; and
   wherein the length of the adjustable leadwire device is adjustable by extending both the first and second coiled insulated wires out of at least one of the first end opening or the second end opening.

11. The adjustable leadwire device of claim 10, wherein a first chest electrode is fixedly attached to the first attachment end and a second chest electrode is fixedly attached to the third attachment end.

12. The adjustable leadwire device of claim 10, wherein the second length of insulated wire is longer than the first length of insulated wire.

13. The adjustable leadwire device of claim 12, further comprising;
   a second helix formed by coiling at least the uncoiled portion of the second length of insulated wire;
   a second sheath around the second helix, wherein the second sheath is configured such that second coiled insulated wire is extendable out of an end opening of the second sheath by pulling the third attachment end.

14. An adjustable leadwire device for connecting a physiological monitor and at least two surface electrodes, the adjustable leadwire device comprising:
   a first length of insulated wire between a first attachment end and a second attachment end;
   a second length of insulated wire between a third attachment end and a fourth attachment end;
   each of the first attachment end and the third attachment end including a first connection means configured to conductively connect to a respective surface electrode;
   the second attachment end and the fourth attachment end connecting to a second connection means configured to conductively connect to the physiological monitor;
   wherein at least a portion of each of the first length of insulated wire and the second length of insulated wire are coiled together so as to form a helix, wherein the second length of insulated wire is longer than the first length of insulated wire such that a portion of the second length of insulated wire is not coiled in the helix;
   a sheath surrounding the helix, the sheath having at least one of a first end opening and a second end opening; and
   wherein the length of the adjustable leadwire device is adjustable by extending both first and second coiled insulated wires out of at least one of the first end opening or the second end opening.

15. The adjustable leadwire device of claim 14, further comprising:
a second helix formed by coiling at least the uncoiled portion of the second length of insulated wire;
a second sheath around the second helix, wherein the second sheath is configured such that second coiled insulated wire is extendable out of an end opening of the second sheath by pulling the third attachment end.

16. The adjustable leadwire device of claim 14, wherein the sheath is configured such that first and second coiled insulated wire is extendable out of at least one of the first end opening or the second end opening by pulling one of the first attachment end and the third attachment end, or by pulling one or the second attachment end or the fourth attachment end in order.

17. The adjustable leadwire device of claim 14, further comprising a first surface electrode connected to the first attachment end and a second surface electrode connected to the third attachment end.

18. A method of making an adjustable leadwire device for connecting at least one surface electrode to a physiological monitor, the method comprising:
providing a length of insulated wire with a first end and a second end;
coiling at least a portion of the length of insulated wire to form a helix;
applying a sheath around the helix; and
forming a first connection means on the first end to create a first attachment end configured to conductively connect to the surface electrode, and forming a second connection means on the second end to create a second attachment end configured to conductively connect to the physiological monitor; and
wherein the sheath is configured such that coiled insulated wire is extendable by pulling a respective one of the first attachment end and the second attachment end in order to adjust a length of the adjustable leadwire device between an initial length when the coiled insulated wire is entirely within the sheath and a maximum length, wherein the initial length is less than or equal to 10% of the maximum length.

19. The method of claim 18, further comprising cutting the sheath covered helix into two or more sections, each section having a first end opening and a second end opening and configured such that the first attachment end extends out of the first end opening of the sheath section and the second attachment end extends out of the second end opening of the sheath section.

20. The method of claim 18, further comprising galvanically connecting a surface electrode to the first connection means.

* * * * *